US009487776B2

(12) United States Patent
List et al.

(10) Patent No.: US 9,487,776 B2
(45) Date of Patent: Nov. 8, 2016

(54) METHOD OF IDENTIFYING MYELODYSPLASTIC SYNDROMES

(75) Inventors: Alan F. List, Tampa, FL (US); Lubomir Sokol, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 13/561,687

(22) Filed: Jul. 30, 2012

(65) Prior Publication Data

US 2012/0316081 A1 Dec. 13, 2012

Related U.S. Application Data

(63) Continuation of application No. PCT/US2011/023170, filed on Jan. 31, 2011.

(60) Provisional application No. 61/299,767, filed on Jan. 29, 2010.

(51) Int. Cl.
 *C12N 15/11* (2006.01)
 *C12Q 1/68* (2006.01)
 *G06F 19/20* (2011.01)

(52) U.S. Cl.
 CPC ........... *C12N 15/111* (2013.01); *C12Q 1/6886* (2013.01); *C12N 2310/141* (2013.01); *C12N 2320/10* (2013.01); *C12Q 2600/118* (2013.01); *C12Q 2600/158* (2013.01); *C12Q 2600/178* (2013.01); *G06F 19/20* (2013.01)

(58) Field of Classification Search
 None
 See application file for complete search history.

(56) References Cited

U.S. PATENT DOCUMENTS

| 7,790,407 B2 | 9/2010 | Ma |
| 2008/0026406 A1 | 1/2008 | Moore et al. |
| 2010/0056608 A1* | 3/2010 | Bjorkegren et al. ........ 514/44 A |

FOREIGN PATENT DOCUMENTS

WO 2011094683 A2 8/2011

OTHER PUBLICATIONS

Wong et al., Real-time PCR for mRNA quantitation; BioTechniques, vol. 39, pp. 75-85, 2005.*
Garzon et al., MicroRNA signatures associated with cytogenetics and prognosis in acute myeloid leukemia; Blood, vol. 111, pp. 3183-3189, 2008.*
Barroga CF, et al., Thrombopoietin regulates c-Myb expression by modulating micro RNA 150 expression. Exp Hematol. 2008;36:1585-1592. Epub Sep. 23, 2009.
Bartel DP., MicroRNAs: Genomics, Biogenesis, Mechanism, and Function. Cell. 2004;116:281-297.
Bellamy WT, et al., Vascular endothelial cell growth factor is an autocrine promoter of abnormal localized immature myeloid precursors and leukemia progenitor formation in myelodysplastic syndromes. Blood. Mar. 1, 2001;97:1427-34.
Bentwich I, et al., Identification of hundreds of conserved and nonconserved human microRNAs. Nat Genet 2005; 37:766-770.
Bernasconi P. Molecular pathways in myelodysplastic syndromes and acute myeloid leukemia: relationships and distinctions—a review. Br J Haematol 2008;142:695-708.
Calin GA, et al., Frequent deletions and down-regulation of micro-RNA genes miR15 and miR16 at 13q14 in chronic lymphocytic leukemia. Proc Nati Acad Sci USA. 2002;99:15524-15529. Epub Nov. 14, 2002.
Calin, GA, et al., Human microRNA genes are frequently located at fragile sites and genomic regions involved in cancers. Proc Natl Acad Sci U S A 2004;101: 2999-3004.
Chen C, et al., Real-time quantification of microRNAs by stem-loop RT-PCR. Nucleic Acid Res. 2005; 33: e179.
Choong, ML, et al. MicroRNA expression profiling during human cord blood-derived CD34 cell erythropoiesis. Exp Hematol 2007; 35, 551-564.
Debernardi S, et al., MicroRNA miR-181a correlates with morphological sub-class of acute myeloid leukaemia and the expression of its target genes in global genome-wide analysis. Leukemia. 2007;21:912-916.
Dore LC, et al., A GATA-1 regulated microRNA locus essential for erythropoiesis. Proc Natl Acad Sci USA 2008;105:3333-3338.
Economopoulou C, et al, Cell cycle and apoptosis regulatory gene expression in the bone marrow of patients with de novo myelodysplastic syndromes (MDS). Ann Hematol. 89, 349-358.
Fabbri M, et al., MicroRNA-29 family reverts aberrant methylation in lung cancer by targeting DNA methyltransferases 3A and 3B. Proc Natl Acad Sci USA 2007;104:15805-15810. Epub Sep. 21, 2007.
Felli N, et al., MicroRNAs 221 and 222 inhibit normal erythropoiesis and erythroleukemic cell growth via kit receptor down-modulation. Proc Natl Acad Sci USA 2005;102:18081-18086.
Fire A, et al., Potent and specific genetic interference by double-stranded RNA in Caenorhabditis elegans. Nature 1998;391:806-811.

(Continued)

*Primary Examiner* — Addison D Ault
(74) *Attorney, Agent, or Firm* — Michele L. Lawson; Robert J. Varkonyi; Smith & Hopen, P.A.

(57) ABSTRACT

Myelodysplastic syndromes display both hematological and biological heterogeneity with variable leukemia potential. To determine whether microRNAs expression offers diagnostic discrimination or influences malignant potential in MDS, bone marrow miRNA expression was investigated from prognostically distinct MDS subsets using a microarray platform. After background subtraction and normalization, data were analyzed indicating thirteen miRNA signature with statistically significant differential expression, including down-regulation of members of a leukemia associated miRNA family. A unique signature consisting of 10 miRNAs was closely associated with International Prognostic Scoring System risk category permitting discrimination between lower and higher risk disease. Selective overexpression of miRNA-181 family members was detected in higher risk MDS, indicating pathogenetic overlap with acute myeloid leukemia. Analysis of miRNA expression profile offers diagnostic utility, and provides pathogenetic and prognostic discimination in MDS.

22 Claims, 5 Drawing Sheets

(56) References Cited

OTHER PUBLICATIONS

Fish JE, et al., MiR-126 regulates angiogenic signaling and vascular integrity. Dev Cel 2008;15:272-284.
Garzon R, et al., MicroRNA-29b induces global DNA hypomethylation and tumor suppressor gene reexpression in acute myeloid leukemia by targeting directly DNMT3A and 3B and indirectly DNMT1.; 2009 113:6411-8. Epub Feb. 11, 2009.
Garzon R, et al., MicroRNA fingerprints during human megakaryocytopoiesis. PNAS 2006;103:5078-5083.
Garzon R, et al., MicroRNA signatures associated with cytogenetics and prognosis in acute myeloid leukemia. Blood. Mar. 15, 2008;111(6):3183-9. Epub Jan. 10, 2008.
Garzon R, Crose CM. MicroRNAs in normal and malignant hematopoiesis. Curr Opin Hematol 2008; 15: 352-358.
Georgantas RW 3rd, Hildreth R, Morisot S, et al., 2007;CD34+ hematopoietic stem-progenitor cell microRNA expression and function: A circuit diagram of differentiation control. Proc Natl Acad Sci USA 104:2750-2755.
Georgantas, RW, et al., CD34+ hematopoietic stem-progenitor cell microRNA expression and function: a circuit diagram of differentiation control. Proc Natl Acad Sci U S A 2007; 104, 2750-2755.
Greenberg P, et al, International scoring system for evaluating prognosis in myelodysplastic syndromes. Blood 89 (6): 2079-88, 1997.
Gubler, U. & Hoffman, BJ. A simple and very efficient method for generating cDNA libraries. Gene. Nov. 1983;25 (2-3):263-9.
Hesse, H, et al. An improved method for generating subtracted cDNA libraries using phage lambda vector. Nuc Acid Res. 1995;23(16):3355-3356.
Jiang Y, et al., Aberrant DNA methylation is a dominant mechanism in MDS progression to AML. Blood. Feb. 5, 2009;113:1315-1325. Epub Oct. 2, 2008.
Johnson SM, et al., RAS is regulated by the let-7 microRNA family. Cell 2005;120:635-647.
Jongen-Lavrencic M, et al., MicroRNA expression profiling in relation to the genetic heterogeneity of acute myeloid leukemia. Blood. May 15, 2008;111(10):5078-85. Epub Mar. 12, 2008.
Labbaye C, et al., A three-step pathway comprising PLZF/miR-146a/CXCR4 controls megakaryopoiesis. Nat Cell Biol 2008;10:788-801.
Le Beau MM, et al., Clinical and cytogenetic correlations in 63 patients with therapy-related myelodysplastic syndromes and acute nonlymphocytic leukemia: further evidence for characteristic abnormalities of chromosomes No. 5 and 7. J Clin Oncol 1986;4:325-45.
List AF, et al, (2004). "Myelodysplastic syndromes." Hematology Am Soc Hematol Educ Program: 297-317.
Liu CG, et al., An oligonucleotide microchip for genome-wide microRNA profiling in human and mouse tissues. Proc Natl Acad Sci USA 2004;101:9740-9744.
Liu SP, et al., MicroRNAs regulation modulated self-renewal and lineage differentiation of stem cells. Cell Transplant 2009;18:1039-1045. Epub Apr. 29, 2009.
Lu J, et al., MicroRNA-mediated control of cell fate in megakaryocyte-erythrocyte progenitors. Dev cell 2008;14:843-853.
Ma X, et al., Myelodysplastic syndromes: incidence and survival in the United States. Cancer 109 (8): 1536-42, 2007.
Marcucci G, et al., Prognostic significance of, and gene and microRNA expression signatures associated with, CEBPA mutations in cytogenetically normal acute myeloid leukemia with high-risk molecular features: a Cancer and Leukemia Group B Study. J Clin Oncol. Nov. 1, 2008;26(31):5078-87.
Marcucci G, et al., MicroRNA expression in cytogenetically normal acute myeloid leukemia. N Engl J Med. May 1, 2008;358:1919-28.
Mi S, et al., MicroRNA expression signatures accurately discriminate acute lymphoblastic leukemia from acute myeloid leukemia. Proc Natl Acad Sci USA 2007; 104: 19971-19976Greenberg P, et al., et al. "International scoring system for evaluating prognosis in myelodysplastic syndromes." Blood 1997; 89: 2079-88.
Mott JL, et al., mir-29 regulates Mcl-1 protein expression and apoptosis. Oncogene 2007;26:6133-6140.
Nuovo GJ, et al., A methodology for the combined in situ analyses of the precursor and mature forms of microRNAs and correlation with their putative targets. Nature Protocols (2009) 4: 107-115.
O'Connell, R.M., et al., Sustained expression of microRNA-155 in hematopoietic stem cells causes a myeloproliferative disorder. J Exp Med 2008; 205, 585-594.
Park SM, et al., Let-7 prevents early cancer progression by suppressing expression of the embryonic gene HMGA2. Cell Cycle 2007;6:2585-2590.
Sampson VB, et al., MicroRNA let-7a down-regulates MYC and reverts MYC-induced growth in Burkitt lymphoma cells. Cancer Res 2007;67:9762-9770.
Simon R, et al., Analysis of Gene Expression Data Using BRB-Array Tools. Cancer Inform 2007; 3, 11-17.
Starczynowski DT, et al., Identification of miR-145 and miR-146a as mediators of the 5q-syndrome phenotype. Nat Med 2010;16:49-58. Epub Nov. 8, 2009.
Yendamuri and Calin, The role of microRNA in human leukemia: a review. Leukemia. Jul. 2009;23(7):1257-63. Epub Jan. 15, 2009.
Tsang WP, Kwok TT. Let-7a microRNA suppresses therapeutics-induced cancer cell death by targeting caspase-3. Apoptosis 2008;13:1215-1222.
Tuncer MA, et al., Primary myelodysplastic syndrome in children: the clinical experience in 33 cases. Br J Haematol 82 (2): 347-53, 1992.
Tusher, et al. Significance analysis of microarrays applied to the ionizing radiation response. Proc Natl Acad Sci USA 2001 98; 5116-5121.
Urbich C, et al., Role of microRNAs in vascular diseases, inflammation, and angiogenesis. Cardiovasc Res 2008;79:551-552.
Volinia S, et al., Reprogramming of microRNA networks in cancer and leukemia. Genome Res 2010; 20, 589-599.
Wang, Y, et al. A simple method for generating full length cDNA from low abundance partial genomic clones. BMC Molecular Biology. 2000, 1:2.
Yamanaka Y, et al., Aberrant overexpression of microRNAs activate AKT signaling via down-regulation of tumor suppressors in natural killer-cell lymphoma/leukemia. Blood 2009;114:3265-3275.
American Cancer Society, Myelodysplastic Syndromes. (2011) Last Medical Review: Jul. 28, 2011; Last Revised Jan. 12, 2012.
Yazji, S. et al. Antithymocyte globulin (ATG)-based therapy in patients with myelodysplastic syndromes. Leukemia. Nov. 2003; 17(11): 2101-6. PMID: 12931212.
Kelaidi and Fenaux. Darbepoetin alfa in anemia of myelodysplastic sydromes: present and beyond. Expert Opin Biol Ther. Apr. 2010; 10(4): 605-14. doi: 10.1517/14712591003709713. PMID: 20201708.
Kantarjian H.M. Therapy of Myelodysplastic Syndrome. Leukemias and Lymphomas. Department of Leukemia, University of Texas MD Anderson Cancer Center. Touch Briefings, 2007. doi: 10.17925/OHR.2007.00.01.66.
Bennett, J.M. Understanding Myelodysplastic Syndromes: A Patient Handbook. 6 Ed. (Myelodysplastic Syndromes Foundation, Inc., 2008).
Myelodysplastic Syndromes Treatment (PDQ). Treatment Options for Myelodysplastic Syndromes. National Cancer Institute. http://www.cancer.gov/types/myeloproliferative/patient/myelodysplastic-treatment-pdq#section/_92, last accessed Aug. 10, 2015.
Myelodysplastic Syndromes Treatment (PDQ). Treatment Option Overview. National Cancer Institute. http://www.cancer.gov/types/myeloproliferative/patient/myelodysplastic-treatment-pdq#section/_49, last accessed Aug. 10, 2015.
Mayo Clinic Staff. Diseases and Conditions. Myelodysplastic syndromes. Treatments and drugs.
Jonasova, Anna et al. Cyclosporin A therapy in hypoplastic MDS patients and certain refractory anaemias without hypoplastic bone marrow. British Journal of Haematology, 1998, 100, 304-309.

* cited by examiner

SEQUENCE LISTING

<160> NUMBER OF SEQ ID NOS: 1

<210> SEQ ID NO 1
<211> LENGTH: 23
<212> TYPE: DNA
<213> ORGANISM: artificial

```
<220> FEATURE:
<223> OTHER INFORMATION: Forward probe

<400> SEQUENCE: 1
acccaccgac agcaatgaat gtt                                               23
```

METHOD OF IDENTIFYING MYELODYSPLASTIC SYNDROMES

CROSS REFERENCE TO RELATED APPLICATIONS

This application is a continuation of International patent application number PCT/US2011/023170 entitled, "Method of Identifying Myelodysplastic Syndromes", filed on Jan. 31, 2011, which is a non-provisional of, and claims priority to U.S. provisional patent application No. 61/299,767, with the same title, filed Jan. 29, 2010 by the same inventors; the contents of which are herein incorporated by reference.

FIELD OF INVENTION

This invention relates to biologic assays. Specifically, the invention provides a method of determining myelodysplastic syndromes using risk-dependent microRNA expression signatures.

BACKGROUND OF THE INVENTION

Myelodysplastic syndromes (MDS) comprise a heterogeneous group of hematopoietic stem cell malignancies that share a high frequency of recurrent chromosomal aberrations and a complex pathogenesis (List A F, et al., (2004). "Myelodysplastic syndromes." Hematology Am Soc Hematol Educ Program: 297-317). MDS malignancies include refractory anemia, refractory cytopenia, myelodysplastic syndrome associated with an isolated del(5q) chromosome abnormality, and unclassifiable myelodysplastic syndrome (National Cancer Institute, General Information About Myelodysplastic Syndromes, 2011). MDS occurs predominantly in older patients, typically over 60 years, though patients as young as 2 years have been reported (Tuncer M A, et al., Primary myelodysplastic syndrome in children: the clinical experience in 33 cases. Br J Haematol 82 (2): 347-53, 1992). Pathogenic mechanisms underlying abnormalities of affected hematopoietic stem cells in MDS remain poorly characterized. Senescence associated accumulation of genetic defects is believed to play a key role in the changes in regulation of apoptosis, differentiation and proliferation potential of affected progenitors (Bernasconi P. Molecular pathways in myelodysplastic syndromes and acute myeloid leukemia: relationships and distinctions—a review. Br J Haematol 2008; 142:695-708). MDS transforms into acute myeloid leukemia (AML) in about 30% of patients after various intervals from diagnosis and at variable rates (National Cancer Institute, General Information About Myelodysplastic Syndromes, 2011).

MDS are diagnosed using an internationally-developed risk analysis, International Prognostic Scoring System (IPSS) for MDS, which analyzed a series of independent risk-based prognostic systems that were combined, collated, and globally analyzed (Greenberg P, et al., International scoring system for evaluating prognosis in myelodysplastic syndromes. Blood 89 (6): 2079-88, 1997). The IPSS uses a multivariate analysis to categorize significant predictors for both survival and AML evolution included bone marrow blast percentage, number of peripheral blood cytopenias, and cytogenetic subgroup, which are used to assign a MDS patient score, which stratifies patients into one of four risk groups: low risk, intermediate-1, intermediate-2, and high risk. The time for the development of AML in the risk groups was 9.4 years, 3.3 years, 1.1 years, and 0.2 years, respectively. Median survival for the groups was 5.7 years, 3.5 years, 1.2 years, and 0.4 years, respectively. MDS is diagnosed in approximately 10,000 people in the United States yearly (Ma X, et al., Myelodysplastic syndromes: incidence and survival in the United States. Cancer 109 (8): 1536-42, 2007).

MicroRNAs (miRNAs) are naturally-occurring, short non-coding RNAs containing 19-25 nucleotides that impair translation or induce mRNA degradation of target mRNA (Fire A, et al., Potent and specific genetic interference by double-stranded RNA in Caenorhabditis elegans. Nature 1998; 391:806-811; Bartel D P., MicroRNAs: Genomics, Biogenesis, Mechanism, and Function. Cell. 2004; 116:281-297). The miRNAs are typically processed from 60- to 70-nucleotide fold-back RNA precursors. Over 500 miRNAs were identified in the human genome (Bentwich I, et al., Identification of hundreds of conserved and nonconserved human microRNAs. Nat Genet 2005; 37:766-770). Analysis of miRNA expression in hematologic malignancies and solid tumors has identified expression patterns that are tumor-type specific with prognostic relevance (Calin G A, et al., Frequent deletions and down-regulation of micro-RNA genes miR15 and miR16 at 13q14 in chronic lymphocytic leukemia. Proc Natl Acad Sci USA. 2002; 99:15524-15529. Epub 2002 Nov. 14; Garzon R, Crose C M. MicroRNAs in normal and malignant hematopoiesis. Curr Opin Hematol 2008; 15: 352-358; Jongen-Lavrencic M, et al., MicroRNA expression profiling in relation to the genetic heterogeneity of acute myeloid leukemia. Blood. 2008 May 15; 111(10): 5078-85. Epub 2008 Mar. 12; Debernardi S, et al., MicroRNA miR-181a correlates with morphological sub-class of acute myeloid leukaemia and the expression of its target genes in global genome-wide analysis. Leukemia. 2007; 21:912-916; Garzon R, et al., MicroRNA signatures associated with cytogenetics and prognosis in acute myeloid leukemia. Blood. 2008 Mar. 15; 111(6):3183-9. Epub 2008 Jan. 10; Marcucci G, et al., Prognostic significance of, and gene and microRNA expression signatures associated with, CEBPA mutations in cytogenetically normal acute myeloid leukemia with high-risk molecular features: a Cancer and Leukemia Group B Study. J Clin Oncol. 2008 Nov. 1; 26(31):5078-8). miRNA expression profiling has shown that myeloblasts from patients with acute myeloid leukemia (AML) display an expression profile that is distinct from normal bone marrow progenitors and acute lymphoblastic leukemia (ALL) (Mi S, et al., MicroRNA expression signatures accurately discriminate acute lymphoblastic leukemia from acute myeloid leukemia. Proc Natl Acad Sci USA 2007; 104: 19971-19976).

Marcucci and colleagues identified a microRNA signature with independent predictive power for event-free survival in cytogenetically normal AML, which included five members of the miR-181 family that target genes involved in erythroid differentiation, homeobox genes and toll-like receptors (Marcucci G, et al., Prognostic significance of, and gene and microRNA expression signatures associated with, CEBPA mutations in cytogenetically normal acute myeloid leukemia with high-risk molecular features: a Cancer and Leukemia Group B Study. J Clin Oncol. 2008 Nov. 1; 26(31):5078-87; Marcucci G, et al., MicroRNA expression in cytogenetically normal acute myeloid leukemia. N Engl J. Med. 2008 May 1; 358:1919-28).

MDS diagnosis requires that MDS be differentiated from other diseases, such as anemia, thromocytopenia, and leukopenia. Therefore, the diagnosis may use blood counts, tests on blood cells to eliminate non-MDS cytopenias, bone marrow examination, and genetic analysis/karyotyping of bone marrow aspirate. Moore, et al. (U.S. application Ser.

No. 11/667,406) discloses methods of comparing the predictive parameters in a blood sample to a control and assigning a numerical score to the values to indicate when a patient suffers from MDS. Moore, et al. looked at surface markers, such as CD66, CD11a, CD10, CD 116, and CD45. Ma (U.S. Pat. No. 7,790,407) analyzed isoforms of SALL4 to determine the likelihood of MDS. However, methods of reliably and accurately diagnosing patients for MDS is still underdeveloped. Accordingly, a method of using miRNA expressions to diagnose and/or prognose the likelihood of MDS is highly desired.

SUMMARY OF INVENTION

The myelodysplastic syndromes (MDS) display both hematological and biological heterogeneity with variable leukemia potential. MicroRNAs (miRNAs) play an important role in tumor suppression and the regulation of self-renewal and differentiation of hematopoietic progenitors. To determine whether miRNA expression offers diagnostic discrimination or influences malignant potential in MDS, bone marrow miRNA expression from prognostically distinct MDS subsets and normal donors was investigated. Using a microarray platform, miRNA expression was evaluated from 44 patients with MDS and 17 age-matched controls. After background subtraction and normalization using a set of housekeeping genes, data were analyzed. An independent set of 18 MDS patients was used to validate the test set signatures using real-time reverse transcriptase polymerase chain reaction (real time RT-PCR). An miRNA gene signature was identified with statistically significant differential expression between normal and MDS specimens (P<0.01), including down-regulation of members of the leukemia associated miRNA let-7 family. These findings were used to develop a method of diagnosing myelodysplastic disease syndrome in a patient. A sample suspected to be cancer is collected from the patient and diagnosed for the existence of myelodysplastic disease syndrome by determining a quantified expression profile of at least one miRNA in a biological sample, where a quantified expression profile is obtained by densitometrically determining the expression of the miRNA, and wherein the at least one miRNA is miR-221 miR-222, miR-29a, miR-29b, miR-10a, miR-196a, miR-320, miR-100, miR124, miR-206, miR-146a, miR-150, miR-326, miR-7e, miR-197, miR-875-5p, miR-181 or combinations thereof. The resulting expression profiles are then compared to the expression profile of the same miRNA or miRNAs obtained from normal donors. In some embodiments, the normal donors are age-matched to the patient. The expression profile of the at least one miRNA is compared using class signatures, Significance Analysis of Microarrays, or threshold cutoffs. The resulting differential expression profile is indicative of presence of myelodysplastic disease syndrome.

The samples are then tested to diagnose the risk level of myelodysplastic disease syndrome. A quantified expression profile of at least one miRNA in a biological sample is again determined by densitometrically determining the expression of the miRNA and compared to expression profiles of corresponding miRNA from normal donors, indicating the risk level of myelodysplastic disease syndrome. During the study, gene expression was compared by International Prognostic Scoring System (IPSS) category (Greenberg P, et al., et al. "International scoring system for evaluating prognosis in myelodysplastic syndromes." Blood 1997; 89: 2079-88) and test set risk signatures were confirmed in a validation set. A unique signature consisting of 10 miRNAs was closely associated with the International Prognostic Scoring System risk category, permitting discrimination between lower (Low/Intermediate-1) and higher risk (Intermediate-2/High) disease (P<0.01). Useful miRNA profiles identified include detecting the oxperexpression of miR-181C, miR-181A, miR-181B, miR-181D, miR-1221, miR-376B, miR-125B, miR-155, miR130A, and underexpression of miR-486-5P to determine an IPSS risk diagnosis. Selective overexpression of miRNA-181 family members was detected in higher risk MDS, indicating pathogenetic overlap with acute myeloid leukemia. Analysis of miRNA expression profile offers diagnostic utility, and provides pathogenetic and prognostic discimination in MDS.

Biological samples can be any tissue sample useful in identifying miRNA expression in circulatory or hematopoietic cells, in particular bone marrow specimens from patients. In some embodiments, mature miRNA is isolated from the sample. The miRNA may be further analysed by using microarrays, locked nucleic acid in situ hybridization, fluorescence in situ hybridization, and other RNA processing methods known in the art. In addition to, or in place of, the RNA processing methods, the RNA may be converted to complementary DNA by subjecting the mature miRNA to reverse transcription PCR. The RNA may also be converted to cDNA by any methods known in the art. Non-limiting examples are readily available (Gubler, U. & Hoffman, B J. A simple and very efficient method for generating cDNA libraries. Gene. 1983 Nov.; 25(2-3):263-9; Wang, Y, et al. A simple method for generating full length cDNA from low abundance partial genomic clones. BMC Molecular Biology. 2000, 1:2; Vaidyanthan, R., et al. Small-RNA transcriptome analysis: a rapid and simple method for generating cDNA from end-tagged RNA. EpiBio. 16(1):1-9; Hesse, H, et al. An improved method for generating subtracted cDNA libraries using phage lambda vector. Nuc Acid Res. 1995; 23(16):3355-3356).

The expression profile may be standardized by background subtraction and normalization using a set of housekeeping genes before comparing the expression profile of the at least one miRNA to those obtained from normal donors. In particular embodiments, the expression profile is standardized using quantiles. Once the RNA or complementary DNA has been processed, the RNA or DNA is analysed to determine the status of the patient. In some embodiments, a cutoff threshold of at least a 1.5 fold change in expression, either up-regulated or down-regulated compared to the miRNA expression from normal donors, indicates the presence of myelodysplastic disease syndrome. The method may also be used to determine whether a patient is at risk to develop myelodysplastic disease syndrome.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
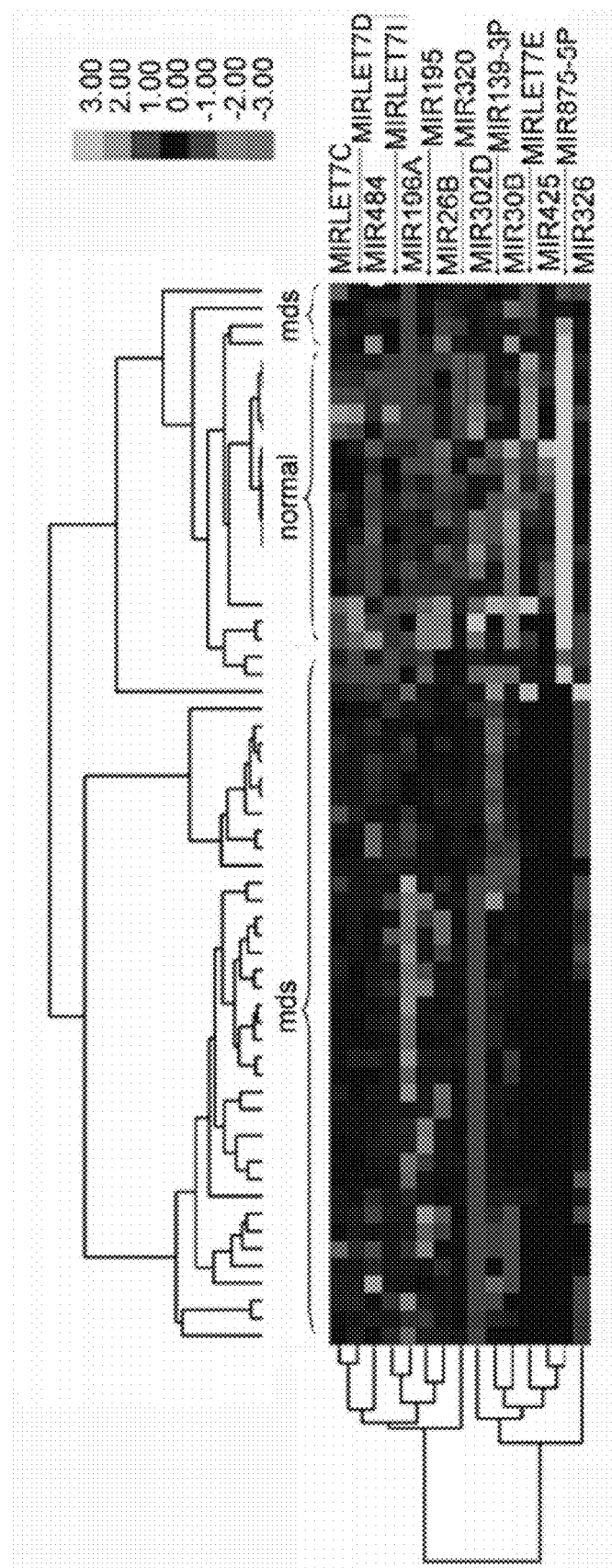
FIG. 1 is an illustration of a heat map showing deregulation of miRNA expression in MDS (n=44) vs. Normal Controls (NC) (n=17). A heat map was generated using the expression ratios of 15 miRNAs selected out of total 73 that differed significantly (p<0.001) according to significance analysis of microarrays (SAM). Light gray (top of scale): up-regulated miRNAs, dark gray (bottom of scale): down-regulated miRNAs. Each column represents a MDS or NC sample, and each row represents a single miRNA. Patient samples are grouped by IPSS.

MicroRNAs (miRNAs) play an important role in tumor suppression and the regulation of self-renewal and differentiation of hematopoietic progenitors. An miRNA gene signature was identified with statistically significant differential expression between normal and myelodysplastic syndromes (MDS) specimens (P<0.01), including down-regulation of members of the leukemia associated miRNA let-7 family. These findings were used to develop a method of diagnosing myelodysplastic disease syndrome in a patient by analyzing a sample suspected to be cancer is collected from the patient through determining the expression of the miRNA, and comparing resulting expression profiles to the expression profile of the same miRNA or miRNAs obtained from normal donors. In some embodiments, the normal donors are age-matched to the patient.

As used herein "patient", means members of the animal kingdom, including mammals, such as but not limited to, primates including humans, gorillas and monkeys; rodents, such as mice, fish, reptiles and birds. The patient may be any animal requiring therapy, treatment, or prophylaxis, or any animal suspected of requiring therapy, treatment, or prophylaxis. The term treatment, as used in this definition only, is intended to mean that regiment described is continued until the underlying disease is resolved, whereas therapy requires that the regiment alleviate one or more symptoms of the underlying disease. Prophylaxis means that regiment is undertaken to prevent a possible occurrence, such as where a pre-cancerous lesion is identified.

As used herein "diagnosing", "diagnose" and "diagnosed" means the evaluation of the presence or properties of existing pathological states, diseases, or conditions. In particular, diagnose means to determine the presence of myelodysplastic disease syndrome in a patient.

As used herein "normal donors" means individuals free of the subject disease, i.e. confirmed not to have or likely to be diagnosed with myelodysplastic disease syndrome.

As used herein "Significance Analysis of Microarrays" and "SAM" is a statistical analysis method, such as the SAM method disclosed in Tusher, et al. (Tusher, et al. Significance analysis of microarrays applied to the ionizing radiation response. Proc Natl Acad Sci USA 2001 98; 5116-5121)

As used herein "quantified", "quantifiable", and "quantify" mean to determine or express the quantity to the test subject through counting and measuring resulting in an objective number.

As used herein "expression profile" is the quantified measurement of the selected the mRNAs.

Forty-four MDS and seventeen normal control (NC) samples of bone marrow mononuclear cells (BMMNC) samples were obtained from Moffitt Cancer Center Tissue Procurement Respository. Written informed consent was obtained from all donors, and laboratory investigations were approved by the institutional review board of the University of South Florida. MDS cases were characterized morphologically according to the World Health Organization (WHO) classification for myeloid malignancies (Swerdlow S H, et al: WHO Classification of tumours of Haematopoietic and Lymphoid Tissues, International Agency for Research on Cancer (IARC), 2008). Prognostic risk was assigned using the International Prognostic Scoring System (IPSS) based on number of cytopenias in peripheral blood, percentage of bone marrow blasts and cytogenetics abnormalities (Greenberg P, et al., "International scoring system for evaluating prognosis in myelodysplastic syndromes." Blood 1997; 89: 2079-88). Clinical and demographic data are summarized in Table 1. Bone marrow mononuclear cells (BM-MNC) were isolated from heparinized bone marrow aspirates on Ficoll-Hypaque gradient and cryopreserved in 20% fetal bovine serum with 10% DMSO. After thawing cells were washed in phosphate-buffered saline before total RNA isolation.

TABLE 1

Patient samples clinical data (Microarray Profiling).

| Sample | Age | Sex | WHO Diagnosis | ISPS | % myeloblast | Cytogenetics |
|---|---|---|---|---|---|---|
| 1 | 55 | M | RARS | 0, LR | 0 | 46, XY |
| 2 | 79 | F | RARS | 0, LR | 0 | 46, XX |
| 3 | 68 | F | RAEB-1 | 0, LR | 2 | 46, XX, del(5)(q13q35)in 3/20 metaphases |

TABLE 1-continued

Patient samples clinical data (Microarray Profiling).

| Sample | Age | Sex | WHO Diagnosis | ISPS | % myeloblast | Cytogenetics |
|---|---|---|---|---|---|---|
| | | | | | | and 46, XX in 17/20 metaphases |
| 4 | 67 | F | RCMD | 0, LR | 2 | 46, XX |
| 5 | 83 | M | RARS | 0, LR | 2 | 46, XY |
| 6 | 74 | M | RARS | 0, LR | 1 | 46, XY |
| 7 | 74 | M | RARS | 0, LR | 1 | 46, XY |
| 8 | 75 | M | RA | 0, LR | 1 | 46, XY |
| 9 | 61 | M | MDS/MPD | 0, LR | 1 | 46, XY |
| 10 | 83 | F | RA | 0, LR | 2 | 46, XX |
| 11 | 68 | M | RARS | 0, LR | 4 | 46, XY |
| 12 | 68 | M | RCMD | 0.5, INT-1 | 5 | 46, XY |
| 13 | 80 | F | RAEB-1 | 0.5, INT-1 | 4 | 46, XX, del(5)(q13q33) |
| 14 | 75 | M | RCMD | 0.5, INT-1 | 1 | 46, XY |
| 15 | 83 | M | RCMD | 0.5, INT-1 | 3 | 46, XY |
| 16 | 64 | M | RA | 0.5, INT-1 | 3 | 46, XY, del(5)(q13q33) |
| 17 | 53 | M | MDS(NOS) | 0.5, INT-1 | 2 | 46, XY |
| 18 | 75 | M | RAEB-1 | 0.5, INT-1 | 6 | 46, XY, del(5)(q13q33) in 19/20 metaphases |
| 19 | 81 | F | RCMD | 0.5, INT-1 | 2 | 46, XX, del(5)(q13q33) |
| 20 | 64 | M | RAEB-1 | 0.5, INT-1 | 7 | 46, XY, del(5)(q13q33) |
| 21 | 69 | M | MDS-NOS | 0.5, INT-1 | 3 | 46, XY |
| 22 | 76 | F | MDS/MPD | 0.5, INT-1 | 5 | 46, XX |
| 23 | 70 | M | RCMD | 0.5, INT-1 | 0 | 46, XY |
| 24 | 68 | M | RAEB-1 | 1.0, INT-1 | 8 | 46, XY, del(5)(q13q33), del (20) (q11.2) |
| 25 | 64 | M | RAEB-1 | 1.0, INT-1 | 6 | 46, XY |
| 26 | 68 | M | RARS | 1.0, INT-1 | 3 | 46, XY |
| 27 | 57 | M | RAEB-2 | 1.0, INT-1 | 1 | 45, XY, del(5)(q13q33), +8, add(11)(p15), −12, −22 in 1/20 metaphases |
| 28 | 35 | M | MDS(NOS) | 1.0, INT-1 | 4 | 7 |
| 29 | 77 | M | RAEB-2 | 1.0, INT-1 | 7 | 46, XY |
| 30 | 61 | F | MDS(NOS) | 1.0, INT-1 | 7 | 45, XX, −7, +mar[4]/46, XX[16]) |
| 31 | 75 | M | RA | 1.0, INT-1 | 10 | 46, XY |
| 32 | 66 | M | RCMD | 1.0, INT-1 | 1 | No mitotic activiity |
| 33 | 77 | M | RA | 1.5, INT-2 | 4 | 44-46, XY, ?Inv(1)(p11.2q21), −4, −4, −5, −6, −11, add(12)(q22), +16, −17, −18, −19, +21, +4, −6 mar |
| 34 | 78 | M | RAEB-2 | 1.5, INT-2 | 14 | 46, XY |
| 35 | 55 | M | RAEB-2 | 1.5, INT-2 | 16 | 46, XY |
| 36 | 65 | M | RAEB-1 | 1.5, INT-2 | 7 | 47, XY, +8[16]/46, XY[4] |
| 37 | 56 | M | RAEB-2 | 1.5, INT-2 | 16 | 46, XY |
| 38 | 84 | M | RARS | 2.0, INT-2 | 3 | 46, XY |
| 39 | 73 | M | RAEB-1 | 2.0, INT-2 | 8 | 46, XY, add(1)(p36), der(3)t(3; ?5)(p12; p1) −5, del(9)(p21), add20(q12), +mar[cp9]/46, XY[11] |
| 40 | 72 | M | RAEB-1 | 2.0, INT-2 | 9 | 45-47, XY, del(1)(q21), −3, del(5)(q13p33) +8, del(12)(p11.2), −18, +20, −21-22, +1-2mar[cp7]/46, XY[13] |
| 41 | 59 | M | RAEB-2 | 2.0, INT-2 | 11 | 46, XY |
| 42 | 71 | F | RAEB-2 | 2.5, HR | 17 | 46, XX, +1, der(1; 7)(q10; P10)[20] |
| 43 | 87 | M | RAEB-1 | 3, HR | 5 | 46, XY, del(5)(q13q32) |

TABLE 1-continued

Patient samples clinical data (Microarray Profiling).

| Sample | Age | Sex | WHO Diagnosis | ISPS | % myeloblast | Cytogenetics |
|---|---|---|---|---|---|---|
| 44 | 83 | M | RAEB-2/ AML | 3.0, HR | 20 | 46, XY, der(5)T(5; 17), −7, −13, −17[cp]/46, XY[3] |

Total RNA was extracted for genome-wide miRNA microarray profiling using QIAzol followed by RNeasy Mini Kit (Qiagen, Valencia, Calif., USA) according to manufacturer instructions. Genome-wide miRNA microarray profiling was performed using a miRNA microarray platform (OSU 3) consisting of 1100 miRNA probes in duplicates including 345 human and 249 mouse miRNA genes. miRNA isolated from hematopoietic cells was biotin-labeled and hybridized on miRNA chips as described elsewhere (Liu C G, et al., An oligonucleotide microchip for genome-wide microRNA profiling in human and mouse tissues. Proc Natl Acad Sci USA 2004; 101:9740-9744). Briefly, 5 μg of total RNA from each sample was reverse transcribed by using biotin end-labeled random octamers. Hybridization was carried out on the custom miRNA microarray chip (with probes (length 40-b) spotted in quadruplicate with annotated active sites. The hybridized chips were washed and processed to detect biotin-containing transcripts by streptavidin-Alexa647 conjugate and scanned by using an Axon 4000B (Axon Instruments, Union City, Calif.). Scanned images of chips were quantified by GENEPIX PRO 6.0 (Axon Instruments). Raw data were normalized using quantiles. miRNA was excluded when less than 20% of expression data had at least a 1.5-fold change in either direction from miRNA's median value.

Statistical comparisons were made using the BRB Array tools (Simon R, et al., Analysis of Gene Expression Data Using BRB-Array Tools. Cancer Inform 2007; 3, 11-17). Expression data were normalized using quantiles. Class comparison between groups of arrays used random variance t tests, which provides improved estimates of gene-specific variances without assuming that all microRNAs have the same variance. The criteria for inclusion of a miRNA is a p-value less than a specified threshold value (i.e. 0.01). For constructing predictors and classifying experiments into classes based on microRNA expression levels we used class prediction in BRB Array tools. Six methods of prediction were applied: compound covariate predictor, diagonal linear discriminant analysis, k-nearest neighbor (using k=1 and 3), nearest centroid, and support vector machines. Class prediction determined cross-validated misclassification rate and performed a permutation test to determine if the cross-validated misclassification rate was lower than it would be expected by chance. The criterion for inclusion of a gene in the predictor was a p-value less than a specified threshold value (i.e. 0.01). The output contains the result of the permutation test on the cross-validated misclassification rate, and a listing of genes that comprise the predictor, with parametric p-values for each microRNA and the CV-support percent (percent of times when the microRNA was used in the predictor for a leave-one-out cross-validation procedure). Heatmaps were produced using centered correlation distance and average linkage with Cluster 3.0 (Stanford Univeristy, School of Medicine, Dept. of Denetics, 2011) and visualized with Java Treeview (Volinia S, et al., Reprogramming of microRNA networks in cancer and leukemia. Genome Res 2010; 20, 589-599). Survival curves were generated using Kaplan-Meier method and the log-rank test to test any difference of survival curves. Holm's method was used to adjust for the two tests. However, other statistical methods may also be used, such as the GeneSpring analysis-of-variance tool, Significance Analysis of Microarray (SAM), and Prediction Analysis of Microarray (PAM).

Real Time RT-PCR was performed using single tube TaqMan MicroRNA Assays to quantify mature microRNAs on Applied Biosystems Real-Time PCR instruments. All reagents, primers and probes were obtained from Applied Biosystems (Applied Biosystems, Foster City, Calif.). RNU48 was used to normalize all RNA samples. Reverse Transcriptase Reactions and Real-Time PCR were performed according to the manufacturer's protocols except that half volumes were used, 7.5 μl for the RT reaction and 10 μl for the PCR reaction, respectively. RNA concentrations were determined with a NanoDrop (NanoDrop Technologies, Inc, Wilmington, Del.). One nanogram RNA per sample was used for the assays. All RT reactions, including no-template controls and RT minus controls, were run in a GeneAmp PCR 9700 Thermocycler (Applied Biosystems). Gene expression levels were quantified using the ABI Prism 7900HT Sequence detection system (Applied Biosystems). Comparative real-time PCR was performed in triplicate, including no-template controls. Relative expression was calculated using the comparative $C_t$ method (Chen C, et al., Real-time quantification of microRNAs by stem-loop RT-PCR. Nucleic Acid Res. 2005; 33: e179). Wilcoxon test was used to compared values between groups, $p<0.05$ was considered significant.

In situ hybridization (ISH) was carried out on deparaffinized bone marrow tissues using a previously published protocol (Nuovo G J, et al., A methodology for the combined in situ analyses of the precursor and mature forms of microRNAs and correlation with their putative targets. Nature Protocols (2009) 4: 107-115), which includes digestion in pepsin (1.3 mg/ml) for 30 minutes. The sequences of the probes containing the six dispersed locked nucleic acid (LNA) modified bases with digoxigenin conjugated to the 5' end were: miR-181-(5') ACC CACC GACAGCAATGAAT-GTT (SEQ ID 1; Exiqon, Inc Woburn, Mass., USA). The probe cocktail and tissue miRNA were co-denatured at 60° C. for 5 minutes, followed by hybridization at 37° C. overnight and a low stringency wash in 0.2×SSC and 2% bovine serum albumin at 4° C. for 10 minutes. The probe-target complex was seen due to the action of alkaline phosphatase on the chromogen nitroblue tetrazolium and bromochloroindolyl phosphate (NBT/BCIP). Negative controls included the use of a scrambled probe. MIRN328 served as a positive control.

miRNA profiles were performed in patients with MDS using a microarray platform. Since a single miRNA is able to regulate multiple genes simultaneously, it is plausible that miRNAs are implicated in pathogenesis of such complex and heterogeneous disorders as MDS. It is hypothesized that deregulation of microRNA expression is most probably initiated in a pluripotent MDS stem cell and subsequently affects more mature bone marrow cells represented in the fraction of bone marrow mononuclear cells. Although it would be optimal to study population of CD34+ cells, this approach was not technically feasible since a microchip platform required 5 ug of total RNA for each sample analysis.

It was found that the miRNA expression profile distinguishes MDS from normal hematopoiesis. miRNA expression was analyzed in 44 MDS patient and 17 age-matched normal control specimens using a miRNA chip (OSU version3). Overall, the MDS cohort included 66% patients with Low/Intermediate-1 risk IPSS categories, and 33% patients with Intermediate-2/High risk disease (Table 1). WHO distribution included refractory anemia (RA) (n=5), refractory anemia with ring sideroblasts (RARS) (n=8), MDS with deletion 5q (n=6), refractory cytopenia with multilineage dysplasia (RCMD) (n=7), refractory anemia with excess blasts-1 (RAEB-1) (n=10) or RAEB-2 (n=8), MDS unclassifiable (MDS-U) (n=4), myelodysplastic/myeloproliferative neoplasm, unclassifiable (MD/MPN-U) (n=2). Overall, 290 miRNAs passed the filtering criterion; among which 42 were up-regulated and 34 down-regulated, as seen in Table 2.

TABLE 2 miRNAs miRNA Expression ProfilingMDS vs. NC.

| miRNA | Parametric p-value | Fold-change | miRNA | Parametric p-value | Fold-change |
|---|---|---|---|---|---|
| | Up-regulated in MDS | | | Down-regulated in MDS | |
| 222 | 0.0020831 | 3.8134893 | 29a* | 0.0498296 | 0.7505738 |
| 10a | 0.0018187 | 3.3731638 | 99b* | 0.0029235 | 0.7131529 |
| 498 | 0.0178186 | 3.1867551 | 671-5p | 0.0209399 | 0.6857212 |
| 196a | 6.66E−05 | 3.0438556 | 135b | 0.0032377 | 0.6744347 |
| 484 | 6.80E−06 | 2.2695246 | 324-3p | 0.0012228 | 0.6720678 |
| 373* | 0.01363 | 2.2545098 | 453 | 0.0054407 | 0.6701189 |
| 487a | 0.0008665 | 2.1452314 | 423-5p | 0.0113928 | 0.6435359 |
| let-7i | 8.12E−05 | 2.1329526 | 497 | 0.0277763 | 0.6246316 |
| 320 | <1e−07 | 2.1178015 | 202* | 0.033228 | 0.62057 |
| 20b | 3.33E−05 | 2.0210908 | 219-5p | 0.027367 | 0.6164717 |
| 16-2* | 0.0012499 | 1.9839672 | 375 | 0.0088289 | 0.609238 |
| 195 | 0.0002391 | 1.9708016 | 323-5p | 0.002739 | 0.5995677 |
| let-7c | 0.0001556 | 1.9698276 | 124* | 0.0009909 | 0.5969912 |
| 190b | 0.001351 | 1.9355495 | 206 | 0.0093797 | 0.5948629 |
| 25 | 0.0082471 | 1.8795849 | 425* | 5.60E−06 | 0.5687575 |
| let-7f | 0.0005667 | 1.8762636 | 146a | 0.0356401 | 0.5652344 |
| let-7d | 0.0002225 | 1.8738434 | 150 | 0.0365018 | 0.5367211 |
| 34a | 0.0024937 | 1.8232345 | 326 | 0.0001276 | 0.5141452 |
| 543 | 0.0436172 | 1.7629473 | 122 | 0.0011772 | 0.5037993 |
| 16 | 0.0062876 | 1.7493375 | 429 | 0.0003291 | 0.4933104 |
| 205 | 0.0011006 | 1.7377885 | 668 | 0.0009988 | 0.4745832 |
| 361-3p | 0.0009668 | 1.6978973 | 7e* | <1e−07 | 0.4631661 |
| 15a | 0.0009378 | 1.6797231 | 151-3p | 0.0008055 | 0.4521857 |
| 135a | 0.0020033 | 1.6623059 | 139-3p | 0.0001406 | 0.4079938 |
| 383 | 0.0232634 | 1.6478122 | 30b* | 6.38E−05 | 0.4052325 |
| 516a-5p | 0.0128898 | 1.6234603 | 124 | 0.0092579 | 0.4005355 |
| 7 | 0.0347966 | 1.6208701 | 424 | 0.0031069 | 0.3881694 |
| 374a | 0.025802 | 1.6078715 | 519d | 0.003383 | 0.3410134 |
| 130a | 0.0243634 | 1.6014545 | 138 | 0.0002496 | 0.3322326 |
| 92a | 0.008479 | 1.5677689 | 197 | 0.000754 | 0.3279825 |
| 191 | 0.0370354 | 1.551769 | 302d | 1.36E−05 | 0.3126365 |
| 185* | 0.0066473 | 1.5253589 | 376b | 0.0005637 | 0.1340773 |
| 100 | 0.0298715 | 1.5061 | 224 | 0.0017198 | 0.1075261 |
| 19b | 0.0367969 | 1.4914713 | 875-5p | <1e−07 | 0.0163577 |
| 193b | 0.0247881 | 1.4713718 | | | |
| 106b | 0.001171 | 1.4582824 | | | |
| 449a | 0.0415588 | 1.4431016 | | | |
| 186 | 0.0265886 | 1.4333901 | | | |
| 374a* | 0.0158386 | 1.4189785 | | | |
| 106a | 0.0204766 | 1.3773127 | | | |
| 196b | 0.0184814 | 1.3393181 | | | |
| 382 | 0.0329346 | 1.3157945 | | | |

Fifteen miRNAs were selected among the 76 miRNAs with differential expression (p<0.001) according to class comparison, from which an expression heat map was constructed (FIG. 1). Using the class prediction, MDS and normal controls were found that had distinct miRNA profiles. A signature consisting of thirteen miRNAs was sufficient to discriminate between these two cohorts (Table 3). Included among these are two down-regulated miRNAs that have key roles in tumorigenesis through deregulation of gene targets such as RAS, MYC, HMGA2 and caspase-3 (MIRNLET7 family) (Johnson S M, et al., RAS is regulated by the let-7 microRNA family. Cell 2005; 120:635-647; Sampson V B, et al., MicroRNA let-7a down-regulates MYC and reverts MYC-induced growth in Burkitt lymphoma cells. Cancer Res 2007; 67:9762-9770; Park S M, et al., Let-7 prevents early cancer progression by suppressing expression of the embryonic gene HMGA2. Cell Cycle 2007; 6:2585-2590; Tsang W P, Kwok T T. Let-7a microRNA suppresses therapeutics-induced cancer cell death by targeting caspase-3. Apoptosis 2008; 13:1215-1222) and stem/progenitor cell self-renewal and maturation potential (MIRN146a, MIRNLET7) (Liu S P, et al., MicroRNAs regulation modulated self-renewal and lineage differentiation of stem cells. Cell Transplant 2009; 18:1039-1045. Epub 2009 Apr. 29; Lab aye C, et al., A three-step pathway comprising PLZF/miR-146a/CXCR4 controls megakaryopoiesis. Nat Cell Biol 2008; 10:788-801); in addition to increased expression of miRNAs that have repressive roles in erythroid (MIRN222) and megakaryocyte (MIRN10a) maturation (Felli N, et al., MicroRNAs 221 and 222 inhibit normal erythropoiesis and erythroleukemic cell growth via kit receptor down-modulation. Proc Natl Acad Sci USA 2005; 102:18081-18086; Garzon R, et al., MicroRNA fingerprints during human megakaryocytopoiesis. PNAS 2006; 103:5078-5083). Of particular interest, MIRN146a is encoded on the long arm of chromosome 5 within the commonly deleted region associated with the 5q-syndrome (Starczynowski D T, et al., Identification of miR-145 and miR-146a as mediators of the 5q-syndrome phenotype. Nat Med 2010; 16:49-58. Epub 2009 Nov. 8). Two of the up-regulated miRNAs are located within homeobox gene clusters that have important roles in hematopoietic development and oncogenesis. MIRN10a and MIRN196-1 are located within the HOX B cluster on 17q21, whereas MIRN196-2 is within the HOX C cluster at 12q13 (Calin, G A, et al., Human microRNA genes are frequently located at fragile sites and genomic regions involved in cancers. Proc Natl Acad Sci USA 2004; 101: 2999-3004).

TABLE 3 miRNA signature differentiating MDS vs. Normal Controls indicate the 13 miRNA signature was predictive (misclassification error rate after 10 fold CV, <0.01).

| miRNA | Status | Fold Change |
|---|---|---|
| 222 | up-regulated | 3.81349 |
| 10a | up-regulated | 3.37316 |
| 196a | up-regulated | 3.04386 |
| 320 | up-regulated | 2.1178 |
| 100 | up-regulated | 1.5061 |
| 124 | down-regulated | 0.59699 |
| 206 | down-regulated | 0.59486 |
| 146a | down-regulated | 0.56523 |
| 150 | down-regulated | 0.53672 |
| 326 | down-regulated | 0.51415 |
| 7e | down-regulated | 0.46317 |
| 197 | down-regulated | 0.32798 |
| 875-5p | down-regulated | 0.01636 |

It was subsequently found that miRNA expression distinguishes higher- from lower-risk MDS. The miRNA expression patterns from 10 patients with higher risk MDS according IPSS score (HR; Int-2/High) were compared to 10 patients with lower risk (LR; low/Int-1) MDS After normalization of data, differences in expression of sixty-eight miRNAs were statistically significant (thirty-eight up-regulated and thirty down-regulated miRNAs, p<0.05), as seen in Table 4.

TABLE 4

MiRNAs Expression Profiling MDS HR vs. LR.

| miRNA | Parametric p-value | Fold-change | miRNA | Parametric p-value | Fold-change |
|---|---|---|---|---|---|
| Up-regulated in HR | | | Down-Regulated in HR | | |
| 181c | <1e−07 | 22.7187 | 363* | 0.038105 | 0.651222 |
| 181a | <1e−07 | 19.94573 | 423-5p | 0.031051 | 0.63736 |
| 181b | 2E−07 | 14.24794 | 124* | 0.028282 | 0.633542 |
| 181d | <1e−07 | 13.87954 | 103 | 0.036724 | 0.629295 |
| 221 | 4E−07 | 12.06954 | 145 | 0.032354 | 0.583281 |
| 220 | 0.000002 | 8.044215 | 193a-5p | 0.01901 | 0.569174 |
| 222 | 0.004875 | 5.161057 | 499-5p | 0.031446 | 0.560958 |
| 376b | 0.024925 | 4.991445 | let-7i | 0.011267 | 0.558375 |
| 18a | 3.75E−05 | 4.449092 | 185 | 0.010333 | 0.55265 |
| 125b | 9E−07 | 4.274317 | 129-5p | 0.009092 | 0.503512 |
| 125a-5p | 0.002883 | 3.902824 | 487a | 0.014127 | 0.489932 |
| 124 | 0.000846 | 3.829622 | 497 | 0.009931 | 0.489157 |
| 155 | 0.000131 | 3.619546 | 342-5p | 0.002583 | 0.469974 |
| 345 | 0.0036 | 3.448313 | 326 | 0.000225 | 0.445401 |
| 519d | 0.019606 | 3.002633 | 370 | 0.048893 | 0.444413 |
| 21 | 0.03621 | 2.963761 | 30c-1* | 0.022059 | 0.43995 |
| 130b | 0.00008 | 2.890153 | 138 | 0.031583 | 0.420103 |
| 32 | 0.002119 | 2.833253 | 500* | 0.016527 | 0.414185 |
| 27a | 0.021457 | 2.826806 | 373* | 0.012698 | 0.378326 |
| 374b | 0.00506 | 2.82613 | 210 | 0.005812 | 0.352821 |
| 130a | 0.000675 | 2.799392 | 136 | 0.002956 | 0.345647 |
| let-7d* | 0.005754 | 2.64277 | 483-3p | 0.000192 | 0.308862 |
| 146a | 0.030923 | 2.637161 | 29b-2* | 0.001647 | 0.305584 |
| 19b | 0.000418 | 2.629067 | 494 | 5.86E−05 | 0.274823 |
| 126 | 0.00857 | 2.512781 | 10a | 0.014823 | 0.274546 |
| 99a | 0.000318 | 2.472185 | 498 | 0.027736 | 0.266855 |
| 194 | 0.013856 | 2.453913 | 876-5p | 0.000308 | 0.181432 |
| 424 | 0.030356 | 2.381149 | 346 | 0.002249 | 0.157089 |
| 361-5p | 0.00206 | 2.297176 | 451 | 0.038564 | 0.136329 |
| 7-1* | 0.004218 | 2.249388 | 486-5p | 0.005686 | 0.118411 |
| 17* | 0.013982 | 2.201785 | | | |
| 128a | 0.028453 | 2.15663 | | | |
| 302d | 0.018448 | 2.143322 | | | |
| 100 | 0.005202 | 2.121136 | | | |
| 30d | 0.016934 | 1.8979 | | | |
| 30e | 0.022858 | 1.856819 | | | |
| 93 | 0.007451 | 1.846122 | | | |
| 27b | 0.044171 | 1.797609 | | | |

Figure 2:
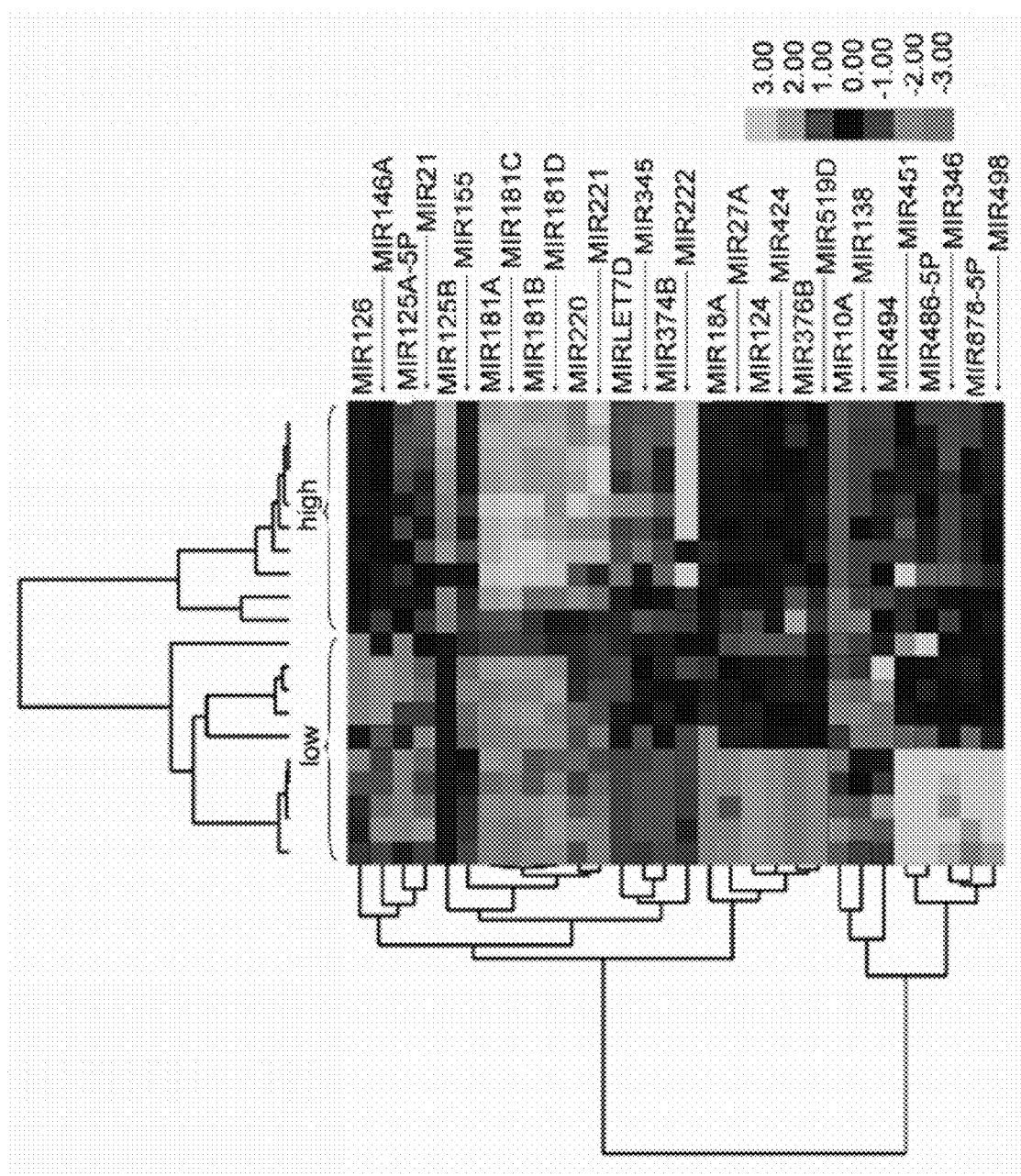
FIG. 2 is an illustration of a heat map showing deregulation of miRNA expression in High Risk (n=10) vs. Low Risk (n=10) MDS patients. A heat map was generated using the expression ratios of 30 miRNAs selected out of total 68 that differed significantly (p<0.05) according to significance analysis of microarrays (SAM). Light gray (top of scale): up-regulated miRNAs, dark gray (bottom of scale): down-regulated miRNAs. Each column represents a patient sample, and each row represents a single miRNA. Patient samples are grouped by IPSS.

Thirty of these miRNAs were selected for heat map construction, seen in FIG. 2. Class predicition analysis identified a unique miRNA signature consisting of 9 up-regulated and 1 down-regulated miRNAs that discriminated the two prognostic groups, as seen in Table 5.

TABLE 5

MiRNA signature differentiating HR vs. LR MDS indicate the signature was predictive (misclassification error rate after 10 fold CV, <0.01) signature was predictive (misclassification error rate after 10 fold CV, <0.01)

| MicroRNA | Status | Parametric P Value | Fold Change | Chromosomal Location |
|---|---|---|---|---|
| MIRN181C | up-regulated | <1e−07 | 22.72 | 19p13.13 |
| MIRN181A | up-regulated | <1e−07 | 19.95 | 19q33.3 |
| MIRN181B | up-regulated | 2E−07 | 14.25 | 1q32.1 |
| MIRN181D | up-regulated | <1e−07 | 13.88 | 19p13.13 |
| MIRN1221 | up-regulated | 4E−07 | 12.07 | Xp11.3 |
| MIRN376B | up-regulated | 0.024925 | 4.99 | 14q32.31 |
| MIRN125B | up-regulated | 9E−07 | 4.27 | 11q24.1 |
| MIRN155 | up-regulated | 0.000131 | 3.62 | 21q21.3 |
| MIRN130A | up-regulated | 0.000675 | 2.80 | 11q12.1 |
| MIRN486-5P | down-regulated | 0.005686 | 0.14 | 8p11.21 |

Figure 3:
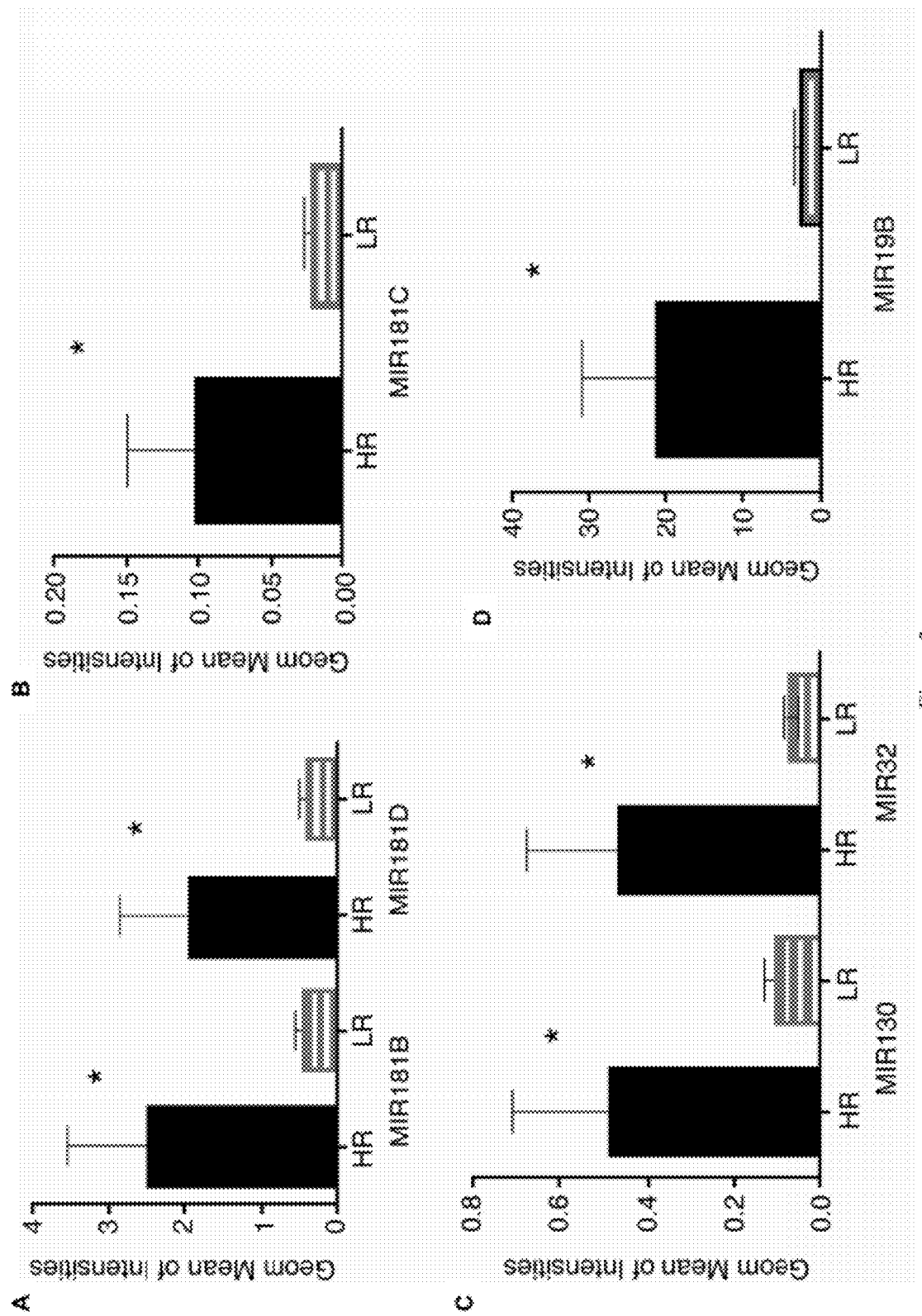
FIG. 3 are graphs showing validation of miRNA expression using independent sample set by Real-Time RT-PCR. Samples from eighteen independent MDS patients (HR=6, LR=12) were analyzed. Seven differentially expressed miR-NAs between HR and LR MDS were selected for Real-Time RT-PCR. Significant correlation was demonstrated for all tested miRNA between miRNA microchip platform and qRT-PCR.
Figure 4:
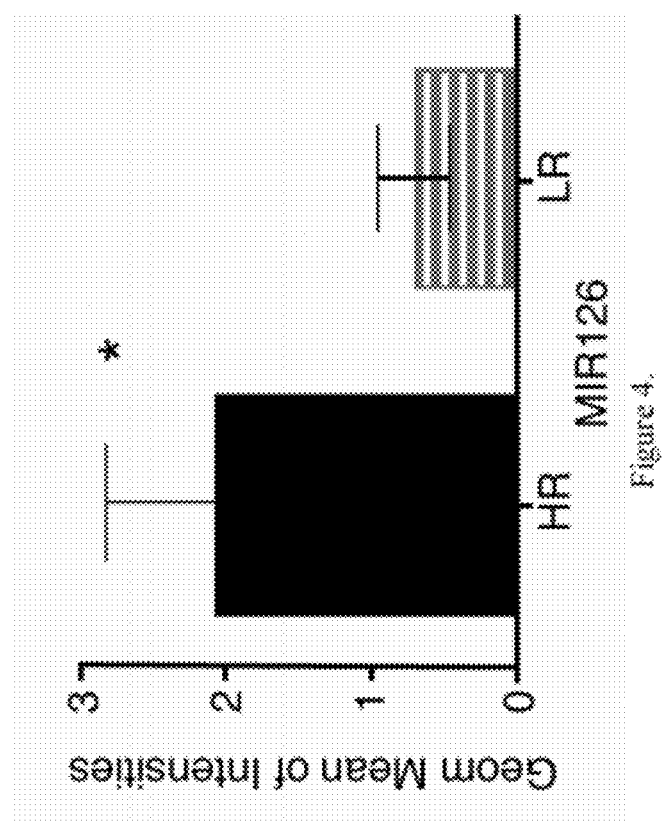
FIG. 4 are graphs showing validation of miRNA expression using independent sample set by Real-Time RT-PCR. Samples from eighteen independent MDS patients (HR=6, LR=12) were analyzed. Seven differentially expressed miR-NAs between HR and LR MDS were selected for Real-Time RT-PCR. Significant correlation was demonstrated for all tested miRNA between miRNA microchip platform and qRT-PCR.

Four members of the MIRN181 family were up-regulated in HR MDS specimens. Results from the microchip platform were validated on an independent set of 18 samples, as seen in Table 6, using quantitative RT-PCR. Expression of seven randomly selected miRNAs was evaluated, as seen in FIG. 3, and confirmed the findings from the microarray chip. Next, expression of MIRN181B was examined in bone marrow biopsies using in situ hybridization with locked nucleic acid (LNA)-modified probes in six bone marrow biopsies from MDS patients and two controls. MIRN181B was strongly expressed in the cytoplasm of HR MDS cells, as seen in FIG. 4, whereas specimens from LR MDS displayed reduced staining intensity. Although a cohort of MDS patients was heterogeneous and included six most common MDS subtypes according to WHO classification, the results suggested that there is an overlap in molecular pathogenesis between these subtypes.

TABLE 6

Patient samples clinical data (Real Time RT-PCR).

| Sample | Age | Sex | WHO Diagnosis | % mieloblast | ISPS | Cytogenetics |
|---|---|---|---|---|---|---|
| 1 | 82 | M | RARS | 2 | 0, LR | 46 X, Y |
| 2 | 71 | F | RARS | 2 | 0, LR | 46, XX |
| 3 | 75 | M | RA | 1 | 0, LR | 46, XY |
| 4 | 75 | M | RA | 1 | 0, LR | 46, XY |
| 5 | 72 | M | RCMD | 2 | 0, LR | 46, XY |
| 6 | 76 | M | RARS | 2 | 0, LR | 46, XY |
| 7 | 76 | F | RARS | 1 | 0, LR | 46 XX |
| 8 | 76 | M | RARS | 2 | 0, LR | 46 XY |
| 9 | 82 | M | RAEB-1 | 2 | 0, LR | 46 XY |
| 10 | 82 | F | RARS | 0 | 0, LR | 46 XX |
| 11 | 69 | M | RCMD | 2 | 0, LR | 46 XY |
| 12 | 73 | M | RARS | 5 | 0, LR | 46 XY |
| 13 | 55 | M | RAEB-1 | 6 | 1.5, INT-2 | 45, XY, −7, der(18)t(8; 18) (p11.2; p11.2) |
| 14 | 68 | M | RCMD | 11 | 2.0, INT-2 | 46, XY |

TABLE 6-continued

Patient samples clinical data (Real Time RT-PCR).

| Sample | Age | Sex | WHO Diagnosis | % mieloblast | ISPS | Cytogenetics |
|---|---|---|---|---|---|---|
| 15 | 73 | M | RAEB-1 | 8 | 2.0, INT-2 | 46, XY, add(1)(p36), der(3)t(3; ?5)(p12; p10), −5, del(9)(p21), add 20)(q12), +mar[cp9]/46, XY[11] |
| 16 | 72 | M | RAEB-1 | 9 | 2.0, INT-2 | 45-47, XY, del(1)(q21), −3, del(5)(q13q33), +8, del(12)(p11.2), −18, +20, −21, −22, +1-2mar [cp7]/46, XY[13] |
| 17 | 70 | M | RAEB-1 | 6 | 2.5, HR | 46, XY |
| 18 | 86 | M | RAEB-2 | 14 | 3.0, HR | 44-45, X, −Y, del(5)(q13q33), del(7)(q22), add(18)(q21), add(21), (p11.2) [13]/46, XY[7] |

Figure 5:
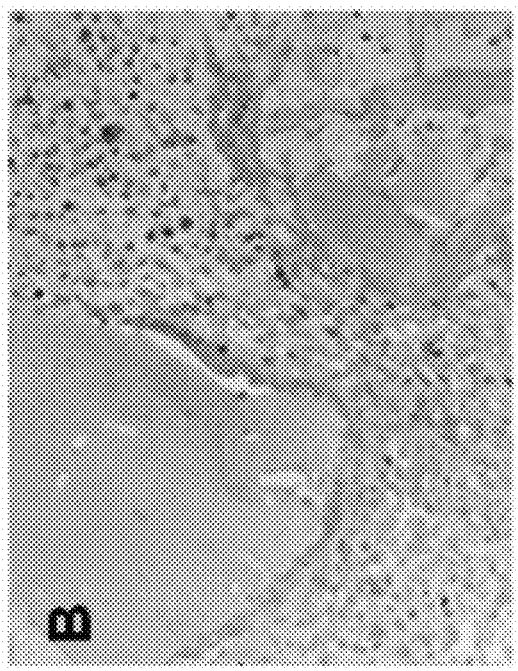
FIG. 5 are histological images. Showing miRNA-181b locked nucleic acid in situ hybridization (LNA-ISH) of formalin fixed, paraffin-embedded bone marrow biopsy sections. 6 patients with MDS and 2 controls were examined. miR-181b is present in the cytoplasm of both A) HR (+++) and B) LR MDS (++) cells arranged in clusters on the background of normal (miRNA-181b negative) hematopoietic cells. C) Negative control—scrambled miRNA probe. D) Positive control—MIRN328.
Figure 5:
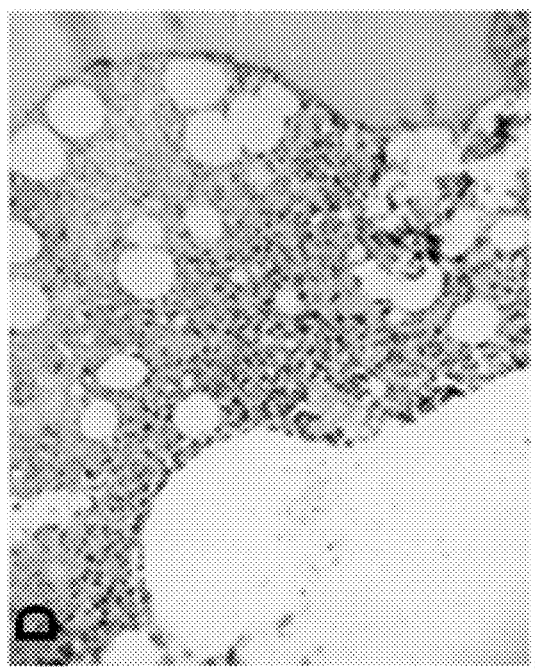
Figure 5:
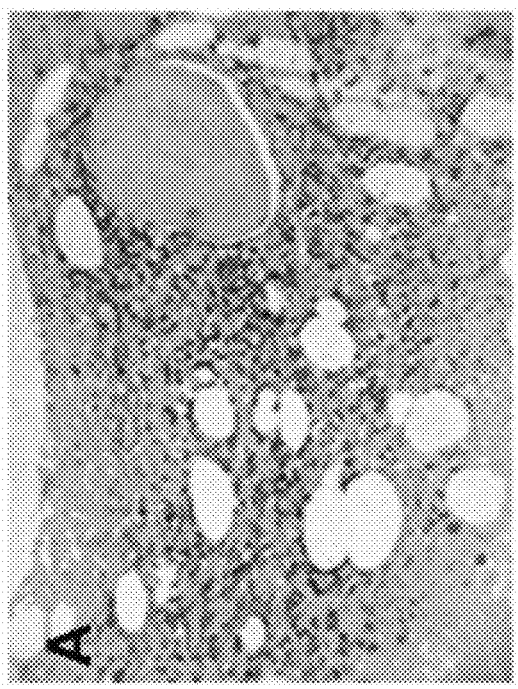
Figure 5:
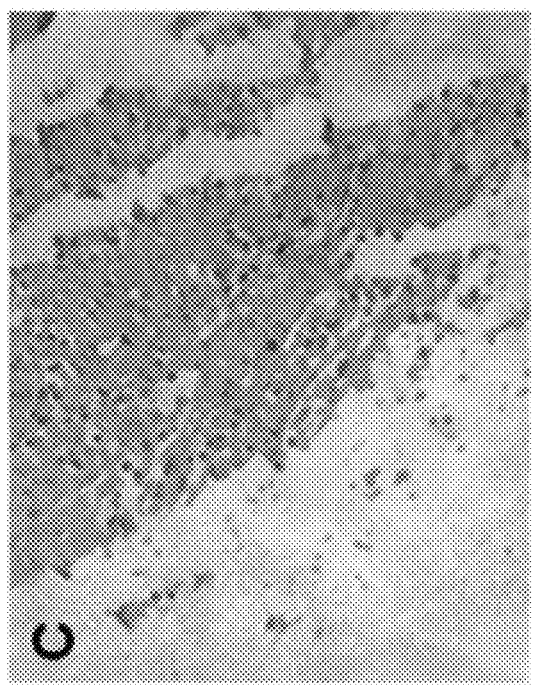

The overall survival in an independent cohort of 22 MDS patients with IPSS lower risk was evaluated. Results of this analysis revealed a significant difference in survival of patients with high expression of MIRN181 family, with a median survival of 3.5 years compared to 9.3 years in patients with low MIRN181 expression (P=0.002), as seen in FIG. 5. Interestingly, two of 3 patients in the data set that developed AML had up-regulation of the MIRN181 family, whereas one did not.

Two microRNA signatures were identified and validated that discriminate MDS from normal control subjects and patients with HR from LR MDS, respectively. A vast majority of microRNAs included in both signatures were previously found to be implicated in regulation of haematopoiesis, apoptosis and angiogenesis.

The MIRN181 family plays an important role in the negative regulation of hematopoiesis including the proliferation and the differentiation of stem/progenitor cells and megakaryocytic lineage development (Georgantas R W 3rd, Hildreth R, Morisot S, et al., 2007; CD34+ hematopoietic stem-progenitor cell microRNA expression and function: A circuit diagram of differentiation control. Proc Natl Acad Sci USA 104:2750-2755). A putative role for MIRN181 in the pathobiology of myeloid malignancies is supported by a recent report by investigators in the Cancer and Leukemia Group B (CALGB) showing that expression of five members of MIRN181 family among a 12 miRNA signature was inversely associated with progression-free survival in AML patients with normal cytogenetics (Marcucci G, et al., MicroRNA expression in cytogenetically normal acute myeloid leukemia. N Engl J. Med. 2008 May 1; 358:1919-28).

Several miRNAs involved in stage-specific control of erythropoiesis (Choong, ML, et al. MicroRNA expression profiling during human cord blood-derived CD34 cell erythropoiesis. Exp Hematol 2007; 35, 551-564; Georgantas, R W, et al., CD34+ hematopoietic stem-progenitor cell microRNA expression and function: a circuit diagram of differentiation control. Proc Natl Acad Sci USA 2007; 104, 2750-2755) were deregulated in MDS. Expression of MIRN221 and MIRN222 normally decline with erythroid maturation to de-repress c-kit expression and facilitate erythroblast expansion (Felli N, et al., MicroRNAs 221 and 222 inhibit normal erythropoiesis and erythroleukemic cell growth via kit receptor down-modulation. Proc Natl Acad Sci USA 2005; 102:18081-18086). Overexpression of these miRNAs, which distinguished MDS patients from age-matched controls in the study, can suppress erythroid growth and may be operative in disease associated ineffective erythropoiesis. The latter may be compounded by down-regulation of members of the MIRN144/451 cluster in HR MDS, which are key transcriptional targets of the erythroid transcription factor GATA-1 and are normally up-regulated with late stages of differentiation (Dore L C, et al., A GATA-1 regulated microRNA locus essential for erythropoiesis. Proc Natl Acad Sci USA 2008; 105:3333-3338). MIRN155, a translational repressor of several myeloid transcription factors including PU.1, C/EPBI3 and CSF1R (Georgantas, R. W., et al., CD34+ hematopoietic stem-progenitor cell microRNA expression and function: a circuit diagram of differentiation control. Proc Natl Acad Sci USA 2007; 104, 2750-2755; O'Connell, R. M., et al., Sustained expression of microRNA-155 in hematopoietic stem cells causes a myeloproliferative disorder. J Exp Med 2008; 205, 585-594), was significantly up-regulated in HR MDS. Mice transplanted with MIRN155-transfected stem cells develop a myeloproliferative disorder with abnormal granulocyte morphology analogous to MDS, suggesting a role in the higher risk MDS phenotype (O'Connell R M, et al., Sustained expression of microRNA-155 in hematopoietic stem cells causes a myeloproliferative disorder. J Exp Med 2008; 205:585-594). Recent investigations have shown that the proliferative effects of MIRN155 are mediated in part through down-regulation of the phosphatase and tensin homologue (PTEN) and consequent up-regulation of the programmed cell death protein 4 (PDCD4), Src homology-2 domain-containing inositol 5-phosphatase 1 (SHIP1) and Akt phosphorylation (Yamanaka Y, et al., Aberrant overexpression of microRNAs activate AKT signaling via down-regulation of tumor suppressors in natural killer-cell lymphoma/leukemia. Blood 2009; 114:3265-3275). Although, not included in the diagnostic signatures, down-regulation of two MIRN29 family members was found in MDS specimens: MiRN29B in HR MDS and MIRN29A in MDS compared to normal controls. Both miRNAs are located on chromosome 7q32, a region commonly deleted in MDS and therapy-related AML (Le Beau M M, et al., Clinical and cytogenetic correlations in 63 patients with therapy-related myelodysplastic syndromes and acute nonlymphocytic leukemia: further evidence for characteristic abnormalities of chromosomes no. 5 and 7. J Clin Oncol 1986; 4:325-45). These MiRNAs target MCL1, a member of the BCL2 anti-apoptotic gene family that is overexpressed in AML and HR MDS (Mott J L, et al., mir-29 regulates Mcl-1 protein expression and apoptosis. Oncogene 2007; 26:6133-6140; Economopoulou C, et al., Cell cycle and apoptosis regulatory gene expression in the bone marrow of patients with de novo myelodysplastic syndromes (MDS). Ann Hematol. 89, 349-358), as well as the DNA methytranferases DNMT-3A and -3B, and indirectly via Sp1, DNMT-1 (Fabbri M, et al., MicroRNA-29 family reverts aberrant methylation in lung cancer by targeting DNA methyltransferases 3A and 3B. Proc Natl Acad Sci USA 2007; 104:15805-15810. Epub 2007 Sep. 21; Garzon R, et al., MicroRNA-29b induces global DNA hypomethylation and tumor suppressor gene reexpression in acute myeloid leukemia by targeting directly DNMT3A and 3B and indirectly DNMT1; 2009 113:6411-8. Epub 2009 Feb. 11). Loss of MIRN29A/B results in overexpression of MCL1 and DNMTs, with corresponding aberrant genomic methylation, suggesting that down-regulation of the MIRN29 family may be a key pathogenetic feature of MDS, and as recently reported, progression of the disease to AML (Jiang Y, et al., Aberrant DNA methylation is a dominant mechanism in MDS progression to AML. Blood. 2009 Feb. 5; 113:1315-1325. Epub 2008 Oct. 2).

Megakaryocytic differentiation of common myeloid progenitors is tightly regulated by the coordinated down-regulation of MIRN10A, -126, -130A and -155, and up-regulation of MIRN150 (Garzon R, et al., MicroRNA fingerprints during human megakaryocytopoiesis. PNAS 2006; 103:5078-5083; Lu J, et al., MicroRNA-mediated control of cell fate in megakaryocyte-erythrocyte progenitors. Dev cell 2008; 14:843-853; Yendamuri and Calin, The role of microRNA in human leukemia: a review. Leukemia. 2009 Jul.; 23(7):1257-63. Epub 2009 Jan. 15). Induction of MIRN150, which suppresses expression of c-myb, is critical for megakaryocytic lineage commitment (Lu J, et al., MicroRNA-mediated control of cell fate in megakaryocyte-erythrocyte progenitors. Dev cell 2008; 14:843-853; Barroga C F, et al., Thrombopoietin regulates c-Myb expression by modulating micro RNA 150 expression. Exp Hematol. 2008; 36:1585-1592. Epub 2009 Sep. 23). These findings of down-regulation of MIRN150 accompanied by up-regulation of MIRN10A in MDS patient specimens compared to normal controls suggests a possible role in dysmegakaryopoiesis and impaired thrombopoiesis in MDS. Interestingly, MIRN155, -126 and -130 were overexpressed in HR-MDS which may further suppress megakaryopoiesis and account for the higher frequency of thrombocytopenia that occurs with disease progression (Garzon R, et al., MicroRNA fingerprints during human megakaryocytopoiesis. PNAS 2006; 103:5078-5083).

The elaboration of angiogenic molecules has been implicated in autocrine cytokine networks supporting myeloid progenitor self-renewal, and in bone marrow microvessel density in HR MDS (Bellamy W T, et al., Vascular endothelial cell growth factor is an autocrine promoter of abnormal localized immature myeloid precursors and leukemia progenitor formation in myelodysplastic syndromes. Blood. 2001 Mar. 1; 97:1427-34). Several up-regulated miRNAs in HR MDS, including MIRN27B, 155, 126, and 130A were previously implicated in regulation of angiogenesis (Urbich C, et al., Role of microRNAs in vascular diseases, inflammation, and angiogenesis. Cardiovasc Res 2008; 79:551-552). In a zebrafish model MIRN126 was shown to control vascular integrity and micro-vessel formation by repressing negative regulators of the vascular endothelial growth factor (VEGF) signaling receptor pathway (Fish J E, et alMiR-126 regulates angiogenic signaling and vascular integrity. Dev Cel 2008; 15:272-284). The data suggest that changes in microRNA expression may promote angiogenesis and lead to MDS disease progression. This work evidences that putative microRNA targets obtained from published literature or from in silico prediction models are implicated in regulation of multiple important pathogenic pathways in haematopoiesis and MDS.

The data reveal that changes in miRNA expression have a fundamental role in the pathogenesis and phenotype of MDS. The vast majority of alterations in miRNA expression affected miRNAs implicated in hematopoiesis and tumorigenesis, as seen in Table 7. MiRNA expression profiling was able to discriminate between normal and MDS hematopoiesis, suggesting that molecular characterization may offer a potentially more rigorous diagnostic alternative to the reliance on morphologic recognition with direct biological implications. Moreover, the identification of miRNA signatures that distinguish IPSS LR from HR MDS indicates that miRNA expression profile also offers prognostic utility that may provide insight into appropriate therapeutic selection. Additionally, MIRN181 expression offers a molecular tool to refine discrimination of disease behavior.

TABLE 7

Deregulated miRNAs in Hematopoiesis in MDS indicate several distinct miRNAs were aberrantly expressed in BM cells derived from erythroid, myeloid and megakaryocytic lineage.

| | Deregulated miRNAs |
|---|---|
| Erythropoiesis | 181, 32, 185, 136, 155, 221, 222, 144, 451 |
| Myelopoiesis | 181, 191, 29b, 29 |
| Megaharyopoiesis | 150, 155, 106, 126, 17, 99 |

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a biomarker for cancer, it will be apparent to those skilled in the art that variations and modifications are possible without deviating from the broad spirit and principle of the present invention. It is intended that all matters contained in the foregoing description or shown in the accompanying drawings shall be interpreted as illustrative and not in a limiting sense. It is also to be understood that the following claims are intended to cover all of the generic and specific features of the invention herein described, and all statements of the scope of the invention which, as a matter of language, might be said to fall therebetween.

What is claimed is:

1. A method of diagnosing and treating myelodysplastic disease syndrome in a patient, comprising:
   collecting a sample suspected to be cancer from the patient;
   detecting the existence of myelodysplastic disease syndrome, further comprising:
      determining a quantified MDS-expression profile in a biological sample, wherein the quantified MDS-expression profile is obtained by:
         generating a plurality of complementary DNA molecules for a plurality of MDS-marker genes from the biological sample;
         contacting at least one complementary DNA molecule to at least one probe for at least one MDS-expression marker gene, wherein the MDS-expression marker gene is miR-222, miR-29a, miR-10a, miR-196a, miR-320, miR-100, miR124, miR-206, miR-146a, miR-150, miR-326, miR-7e, miR-197, miR-875-5p, let-7i, let-7c, let-7f, let-7d, or combinations thereof;
         quantifying the at least one MDS-marker gene to generate the at least one MDS-expression profile;
      comparing the quantified MDS-expression profile to a MDS-control profile obtained from normal donors to form a differential MDS-expression profile;
      wherein the MDS-control profile is obtained by determining the expression of the at least one MDS-expression marker gene in the normal donors;
      wherein the differential MDS-expression profile is indicative of presence of myelodysplastic disease syndrome when showing at least upregulation of miR-10a, miR-100, miR-196, miR-222, miR-320, let-7i, miR-320, let-7c, let-7f, let-7d, or miR-100, or downregulation of miR-7e, miR-29a, miR-124, miR-146a, miR-150, miR-197, miR-206, miR-326, or miR-875-5p, and
   determining the risk level of myelodysplastic disease syndrome, further comprising:
      determining a quantified risk-expression profile in a biological sample, wherein the quantified risk-expression profile is obtained by:
         contacting at least one complementary DNA molecule to at least one probe for at least one risk-expression marker gene, wherein the risk-expression marker gene is miR126, miR125a-5p, miR21, miR125b, miR155, miR181a, miR181b, miR181c, miR181d, miR220, miR345, miR374b, miR18a, miR27a, miR424, miR376b, miR519d, miR138, miR494, miR451, miR486-5p, miR346, miR878-5p, miR498, miRN1221, miRN130a, or a combination thereof;
         quantifying the at least one risk-expression marker gene to generate the quantified risk-expression profile;
      comparing the quantified risk-expression profile of the biological sample to a quantified risk-control profile obtained from nucleic acids from age-matched control donors;
      assigning a risk score based on variation between the risk-expression profile and the risk-control profile;
      wherein the risk score is assigned by
         assigning 1 point where the risk expression profile varies from the risk-control profile by 1-2 standard deviations and 2 points where the risk expression profile varies from the risk-control profile by over 2 standard deviations, or assigning 1 point where the risk expression profile varies from the risk-control profile by more than a threshold value, where the threshold value is a p value of 0.01 or a 1.5-fold change of the risk-control profile;
         summing the points to obtain a risk score;
      wherein a risk score of 2 or more is indicative of a high risk level of myelodysplastic disease syndrome; and
   administering a treatment for myelodysplastic disease syndrome when the risk score is 2 or more, where the treatment for myelodysplastic disease syndrome is blood transfusion, platelet transfusion, non-myeloblative bone marrow transplant, administration of granulocyte colony-stimulating factor, erythropoiesis-stimulating agent, epogen, darbopoietin alpha, anti-thymocyte globulin, cyclosporine A, corticosteroid, lenalidomide, azacitidine, 5-azacytidine, low-dose chemotherapy, thalidomide, arsenic trioxide, or decitabine.

2. The method of claim 1, wherein the biological sample is a bone marrow specimen collected from the patient.

3. The method of claim 1, wherein the expression of miRNA in a biological sample is determined using a microarray platform.

4. The method of claim 1, further comprising standardizing the expression profile by background subtraction and normalization using a set of housekeeping genes before comparing the expression profile of the at least one miRNA to those obtained from normal donors.

5. The method of claim 4, wherein the expression profile is standardized using quantiles.

6. The method of claim 1, further comprising isolating mature miRNA from the sample.

7. The method of claim 6, further comprising obtaining complementary DNA from the mature miRNA by subjecting the mature miRNA to reverse transcription PCR.

8. The method of claim 1, wherein the at least one miRNA used to diagnose the risk level of myelodysplastic disease syndrome is miR-181a, miR-181b, miR-181c, miR-181d, miR-1221, miR-376b, miR-125B, miR-155, miR130a, and miR-486-5p.

9. The method of claim 1, wherein the miRNA has at least a 1.5 fold change in expression compared to the miRNA expression from normal donors, indicating the presence of myelodysplastic disease syndrome.

10. The method of claim 1, further comprising standardizing the expression profile by background subtraction and normalization using a set of housekeeping genes before comparing the expression profile of the at least one miRNA to those obtained from normal donors.

11. The method of claim 1, wherein the at least one miRNA used to detect the existence of myelodysplastic disease syndrome is miR-222, miR-10a, miR-196a, miR-320, miR-100, miR124, miR-206, miR-146a, miR-150, miR-326, miR-7e, miR-197, and miR-875-5p.

12. The method of claim 1, wherein a risk score of 3 or more is indicative of the risk level of myelodysplastic disease syndrome.

13. The method of claim 1, wherein the treatment for myelodysplastic disease syndrome is platelet transfusion, blood transfusion, non-myeloblative bone marrow transplant, low-dose chemotherapy, 5-azacytidine, thalidomide, arsenic trioxide, or azacitidine.

14. A method of predicting myelodysplastic disease syndrome in a patient, comprising
collecting a biological sample suspected to be cancer from the patient;
detecting the existence of myelodysplastic disease syndrome, further comprising:
determining a quantified MDS-expression profile in the biological sample, wherein the quantified MDS-expression profile is obtained by:
generating a plurality of complementary DNA molecules for a plurality of MDS-marker genes from the biological sample;
contacting at least one complementary DNA molecule to at least one probe for at least one MDS-expression marker gene, wherein the MDS-expression marker gene is miR-222, miR-29a, miR-10a, miR-196a, miR-320, miR100, miR124, miR-206, miR-146a, miR-150, miR-326, miR-7e, miR-197, miR-875-5p, let-7i, let-7c, let-7f, let-7d, or combinations thereof;
quantifying the at least one MDS-marker gene to generate the quantified MDS-expression profile;
comparing the quantified MDS-expression profile to a MDS-control profile obtained from normal donors to form a differential MDS-expression profile using class signatures or Significance Analysis of Microarrays;
wherein the MDS-control profile is obtained by determining the expression of the at least one MDS-expression marker gene in the normal donors;
wherein the differential MDS-expression profile is indicative of presence of myelodysplastic disease syndrome when showing at least upregulation miR-10a, miR-100, miR-196, miR-222, miR-320, let-7i, miR-320, let-7c, let-7f, let-7d, or miR-100, or downregulation of miR-7e, miR-29a, miR-124, miR-146a, miR-150, miR-197, miR-206, miR-326, or miR-875-5p; and
determining the risk level of myelodysplastic disease syndrome, further comprising:
determining a quantified risk-expression profile of a plurality of risk-expression markers in the biological sample, where the quantified risk-expression profile is obtained by:
contacting at least one complementary DNA molecule to a plurality of risk-expression markers, wherein the risk-expression markers are selected from miR-181c, miR-181a, miR-181b, miR-181d, miR-1221, miR-376b, miR-125b, miR-155, miR-130a, and miR-486-5p;
measuring expression of the at least one risk-expression marker contacted with the at least one complementary DNA molecule to generate the quantified risk-expression profile;
comparing the at least one risk-expression profile of the biological sample to a quantified risk-control profile obtained from nucleic acids from age-matched control donors;
assigning a risk score based on variation between the quantified risk-expression profile and the risk-control profile;
wherein the risk score is assigned by
assigning 1 point where the risk expression profile varies from the risk-control profile by 1-2 standard deviations and 2 points where the quantified risk expression profile varies from the risk-control profile by over 2 standard deviations, or assigning 1 point for variation above a threshold value, where the threshold value is a p value of 0.01 or a 1.5-fold change of the risk-control profile;
summing the points to obtain a risk score;
wherein a risk score of 2 or more is indicative of a high risk level of myelodysplastic disease syndrome; and
administering a treatment for myelodysplastic disease syndrome when the risk score is 2 or more, where the treatment for myelodysplastic disease syndrome is blood transfusion, administration of granulocyte colony-stimulating factor, erythropoiesis-stimulating agent, epogen, darbopoietin alpha, anti-thymocyte globulin, cyclosporine A, corticosteroid, lenalidomide, azacitidine, decitabine, platelet transfusion, platelet transfusion, non-myeloblative bone marrow transplant, low-dose chemotherapy, 5-azacytidine, thalidomide, azacytidine or arsenic trioxide.

15. The method of claim 14, wherein the plurality of complementary DNA molecules was generated from the mature miRNA by subjecting the mature miRNA to reverse transcription PCR.

16. The method of claim 14, wherein the biological sample is a bone marrow specimen collected from the patient.

17. The method of claim 14, wherein the expression of miRNA in a biological sample is determined using a microarray platform.

18. The method of claim 10, wherein the expression profile is standardized using quantiles.

19. The method of claim 14, wherein the at least one miRNA used to detect the existence of myelodysplastic disease syndrome is miR-222, miR-10a, miR-196a, miR-320, miR-100, miR124, miR-206, miR-146a, miR-150, miR-326, miR-7e, miR-197, and miR-875-5p.

20. The method of claim 14, wherein a risk score of 3 or more is indicative of the risk level of myelodysplastic disease syndrome.

21. The method of claim 16, wherein the bone marrow specimen is a mononuclear cell fraction.

22. The method of claim 14, wherein the treatment for myelodysplastic disease syndrome is platelet transfusion, blood transfusion, non-myeloblative bone marrow transplant, low-dose chemotherapy, 5-azacytidine, thalidomide, arsenic trioxide, or azacitidine.

* * * * *